United States Patent [19]

Melker et al.

[11] Patent Number: 5,250,038
[45] Date of Patent: Oct. 5, 1993

[54] MULTIPLE LUMEN VASCULAR ACCESS INTRODUCER SHEATH

[75] Inventors: Richard J. Melker, Gainesville, Fla.; Frank J. Fischer, Jr., Bloomington, Ind.

[73] Assignee: Cook Incorporated, Bloomington, Ind.

[21] Appl. No.: 959,289

[22] Filed: Oct. 9, 1992

[51] Int. Cl.$^5$ ............................................. A61M 5/00
[52] U.S. Cl. ..................... 604/264; 604/167; 604/283
[58] Field of Search ................ 604/264, 164–170, 604/52, 53, 280, 283, 284

[56] References Cited

U.S. PATENT DOCUMENTS

| | | | |
|---|---|---|---|
| 4,073,297 | 2/1978 | Kopp | 604/167 |
| 4,299,217 | 11/1981 | Sagae et al. | 604/167 X |
| 4,406,656 | 9/1983 | Hattler et al. | 604/280 |
| 4,968,307 | 11/1990 | Dake et al. | 604/264 |
| 5,029,580 | 7/1991 | Radford et al. | 128/207.14 |

*Primary Examiner*—John D. Yasko
*Attorney, Agent, or Firm*—Richard J. Godlewski

[57] ABSTRACT

A multiple lumen vascular access introducer sheath having a main lumen for introduction of another device such as a catheter therethrough and into the vascular system and a secondary lumen having a cross-sectional area significantly less than that of the main lumen for infusion of small doses of medication therethrough at a controlled rate and directly into the vascular system. The introducer sheath comprises a tubular member of an inelastic, semi-rigid plastic material such as fluorinated ethylene propylene or nylon. The main lumen extends longitudinally through the tubular member and opens at the distal and proximal ends thereof. The secondary lumen is positioned adjacent to and separated from the main lumen with a cross-sectional area approximately fifteen percent of that of the main lumen. The distal end of the tubular member is tapered with the distal end of the secondary lumen closed. The secondary lumen has a side port near the tapered distal end. The sheath also includes a hub with main and secondary passages communicating with the main and secondary lumens of the tubular member. The longitudinal axes of the main passages are substantially parallel to one another. The secondary passage extends laterally from the secondary lumen of the tubular member which is recessed from the proximal end thereof. The hub also includes a third passage communicating with and extending laterally from the main lumen of the tubular member.

20 Claims, 1 Drawing Sheet

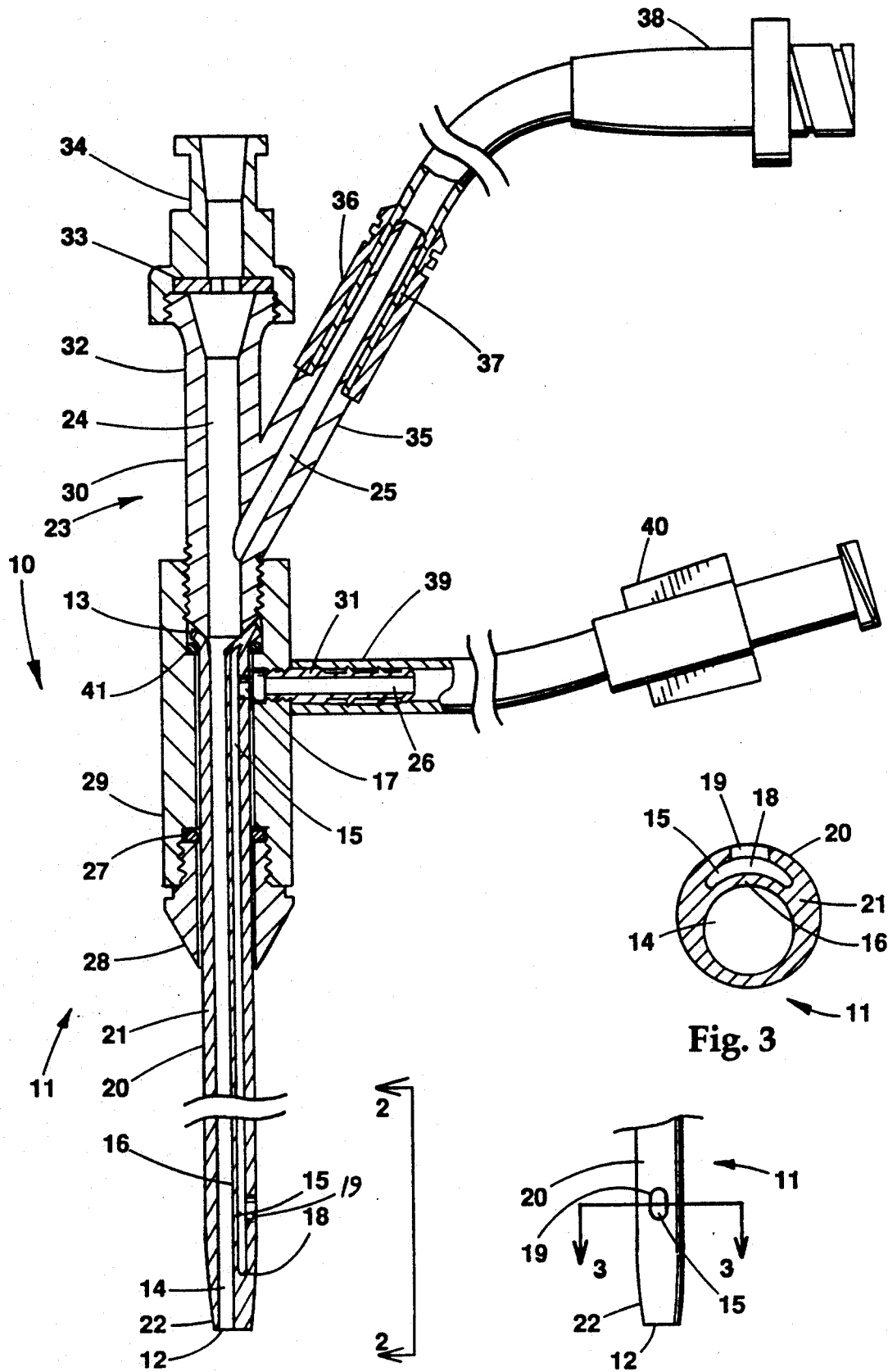

MULTIPLE LUMEN VASCULAR ACCESS INTRODUCER SHEATH

CROSS-REFERENCE TO RELATED APPLICATION(S)

This application is related to application Ser. No. 07/959,287, entitled "A Vascular Wire Guider Introducer and Method of Use", filed concurrently herewith and assigned to a common assignee.

TECHNICAL FIELD

This invention relates generally to vascular access introducer sheaths and, in particular, to a vascular access introducer sheath with multiple lumens, a first one for passing a catheter therethrough and another separated from the first for passing a small amount of a fluid therethrough.

BACKGROUND OF THE INVENTION

It is often desirable to maintain vascular access with a device that simultaneously accommodates multiple use such as the insertion of various devices and the injection or withdrawal of fluids. In emergency and critical care situations, urgently needed medication can be injected through the lumen of an introducer sheath, which already provides for passage of wire guides, catheters, and other devices. Injecting an emergency dose of medication through the introducer sheath at an established vascular access site eliminates the potentially life-threatening time delay of obtaining an additional site. Furthermore, a patient may not have another usable site for vascular access. Therefore, it is desirable that a vascular access introducer sheath be capable of supporting multiple applications and, in particular, simultaneously accommodating the insertion of devices and the injection of fluids, particularly at a controlled infusion rate.

Several possible solutions have been suggested for simultaneously supporting multiple applications. One solution is the use of a single-lumen introducer sheath. A problem with this introducer sheath is that the wire guide or catheter positioned through the lumen occludes the lumen and obstructs the passage of fluid through the lumen. As a result, a small amount of injected medication requires a relatively large "push" of another fluid such as saline to facilitate forcing the medication to the distal end of the sheath. A single-lumen introducer sheath can also include a side port positioned about the proximal end thereof. A proximally positioned side port provides a second avenue of entry to the introducer sheath lumen, but the above-mentioned problem with having only a single lumen remains. Another problem with the side port is that there is dead space in the side port fitting at the proximal end of the sheath lumen where medication and fluids pool. A relatively large "push" of saline dilutes the small dose of medication already backed up and remaining in the dead space. As a result, the "push" serves to force very little medication to the distal end of the sheath and into the bloodstream of a patient. There is also another major problem with single-lumen introducer sheaths, particularly when attempting to infuse medication at a controlled rate. The insertion and withdrawal of devices through a single-lumen introducer sheath interrupts the infusion of medication at a controlled rate, which can be life threatening. Therefore, a single-lumen introducer sheath provides an inefficient means, at best, for the simultaneous passage of various devices and infusion of medication, particularly at a controlled rate.

Another possible solution is the use of a multi-lumen catheter. A problem with using a multi-lumen catheter is that the catheter is typically inserted into the vascular system through an introducer sheath. As a result, there is a time delay for initiating vascular access during the start-up of a procedure, which is particularly critical in an emergency or intensive care situation. Another problem with using a multi-lumen catheter is that the outside diameter of the catheter is significantly larger than that of a single-lumen catheter. As a result, a larger introducer sheath is used, and a larger opening is made in the patient's blood vessel. This large blood vessel opening causes a greater loss of blood and increased risk of complications that may be life threatening in surgical or emergency situations. Alternatively, if the outside diameter of a multi-lumen catheter is desirably small, the lumens of an elastic, soft plastic material catheter are also small, which severely limits the range of devices that can be passed through the catheter.

SUMMARY OF THE INVENTION

The foregoing problems are solved and a technical advance is achieved in an illustrative multiple lumen vascular access introducer sheath having a main lumen for passage of a catheter therethrough and a secondary lumen positioned adjacent to and separated from the main lumen and having a cross-sectional area significantly less than that of the main lumen for advantageously passing a relatively small dose of a fluid, such as a medication, therethrough. This advantageously allows small doses of medication to be injected without large "pushes" of another fluid such as saline to deliver the medication to the distal end of the sheath and the vascular system. Dead space in the lumen and proximal end fitting is minimized. Furthermore, medication can be infused at a controlled rate while another device, such as a guide wire or catheter, remains in, is inserted into, or is withdrawn from the main lumen of the introducer sheath.

The introducer sheath comprises a tubular member of an inelastic, semi-rigid plastic material and a main lumen extending longitudinally therethrough and opening at the distal and proximal ends thereof. The plastic material preferably has a molten state to form the tapered distal end of the sheath and is from a group consisting of fluorinated ethylene propylene and nylon. The tubular member includes an outer wall surrounding the main and secondary lumens and an inner wall separating the main and secondary lumens. The secondary lumen is closed at the tapered distal end of the tubular member and includes a side port in the outer wall near the tapered distal end of the tubular member for advantageously injecting fluids directly into the vascular system. The cross-sectional area of the main lumen has a circular shape, whereas the secondary lumen of the tubular member has at least a partially crescent shape for maximizing the effective cross-sectional area of the introducer sheath while minimizing the outside diameter of the introducer sheath. The cross-sectional area of the secondary lumen is approximately fifteen percent of the cross-sectional area of the main lumen. This also advantageously reduces the dead space of the secondary lumen of the introducer sheath while maximizing the inside diameter of the main lumen for passage of other medical devices therethrough.

The introducer sheath further comprises a hub attached about the proximal end of the tubular member. The hub has a main passage extending longitudinally therethrough and communicating with the main lumen of the tubular member. The longitudinal axes of the hub main passage and the member main lumen are substantially parallel for readily introducing other devices therethrough and into the vascular system. The secondary lumen of the tubular member has a proximal opening recessed from the proximal end of the tubular member. The hub has a secondary passage, which communicates with the secondary lumen of the tubular member and extends laterally from the main passage of the hub and the secondary lumen of the tubular member. The hub also advantageously includes a third passage, which communicates with and extends laterally from the main lumen of the tubular member, for injecting fluids into the main lumen of the introducer sheath with another medical device introduced through the main passage and lumen.

BRIEF DESCRIPTION OF THE DRAWING

FIG. 1 depicts a partially-sectioned side view of a multiple lumen vascular access introducer sheath of the present invention;

FIG. 2 depicts an enlarged side view of the distal end of the sheath of FIG. 1 along the line 2—2; and FIG. 3 depicts a cross-sectional view of the distal end of the sheath of FIG. 2 along the line 3—3.

DETAILED DESCRIPTION

FIG. 1 depicts an illustrative multiple lumen vascular access introducer sheath 10 for the infusion of small doses of fluids, particularly at a controlled rate, and the introduction of medical devices such as catheters or wire guides therethrough and into the blood vessel of a patient. Sheath 10 comprises tubular member 11 with distal end 12, proximal end 13, and main lumen 14, which extends longitudinally therethrough and opens at the distal and proximal ends for positioning medical devices therein. Main lumen 14 has a generally circular and relatively large cross-sectional area for accommodating a range of medical devices and providing for the rapid delivery of large amounts of fluid such as saline, blood plasma, or whole blood. Tubular member 11 further includes secondary lumen 15, which is positioned adjacent main lumen 14 and is separated therefrom by inner wall 16. Secondary lumen 15 extends longitudinally through the tubular member from at least closed distal end 18 to proximal side port opening 17 that is cut or drilled near proximal end 13 of the tubular member. Secondary lumen 15 has an at least partially crescent shape and a significantly smaller cross-sectional area than that of the main lumen. The secondary lumen has a cross-sectional area comprising, for example, approximately 15 percent of that of the main lumen for minimizing dead space during injection of a predetermined dosage of fluid medication. Secondary lumen 15 opens distally at distal side port 19 formed in outer wall 20 of the tubular member, as depicted in FIG. 2.

Tubular member 11 is formed of inelastic, semi-rigid plastic material 21 that includes a molten state such as nylon or fluorinated ethylene propylene. The molten state of the plastic material provides for taper 22 to be formed in distal end 12 of the tubular member for presenting an atraumatic surface to a blood vessel wall.

Sheath 10 further comprises hub 23 fixedly attached about proximal end 13 of the tubular member. Hub 23 comprises distal connector 28, intermediate connector 29, proximal Y-fitting 30, and lateral fitting 31. The distal connector and proximal Y-fitting are threadably attached and secured with a commercially available medical grade adhesive to the opposite ends of the intermediate connector. Hub 23 includes main passage 24, which extends through main arm 32 of the Y-fitting and has a longitudinal axis that is at least substantially parallel to the longitudinal axis of main lumen 14 of the tubular member. In this way, main lumen 14 communicates with main passage 24 for in-line introduction of devices or fluid therethrough. Main arm 32 includes male luer lock fitting 34 for lockable attachment to a syringe or another medical device and check valve 33 comprising, for example, a slotted silicone seal.

Hub 23 further includes side-arm passage 25 positioned in side arm 35 of Y-fitting 30 for communicating with main lumen 14 and extending laterally from the longitudinal axis of the main lumen. Side-arm passage 25 provides for the introduction of fluid into the main lumen of the tubular member when another medical device extends from the main lumen through main passage 24 of the hub. For convenient accessibility, extension tube 37 is positioned over side arm 35 and secured thereto by outer tubular connector 36, which is compression-fitted thereover. Extension tube 37 includes well-known male threaded connector 38 positioned at the proximal end thereof.

Hub 23 also further includes secondary passage 26 positioned in lateral fitting 31 and communicating with secondary lumen 15 via intermediate connector 29 and proximal opening 17. Secondary passage 26 extends laterally from the longitudinal axis of the main and secondary lumens of the tubular member. Lateral fitting 31 includes external threads about its distal end for being threadably affixed to intermediate connector 31. Extension tube 39 is positioned about the barbed outer surface of lateral fitting 31 and includes male luer lock fitting 40 about the proximal end thereof.

Distal O-ring 27 is positioned in intermediate connector 29 about outer wall 20 of the tubular member and distal to the intersection of secondary lumen 15 and secondary hub passage 26 for preventing leakage of fluid from the communicating passageways. Proximal O-ring 41 is positioned in intermediate connector 29 about the outer surface of the tubular member. Proximal O-ring 41 is sized smaller than the distal O-ring for compressing about the tubular member and collapsing the secondary lumen to prevent retrograde fluid flow and leakage from secondary lumen 15 and secondary hub passage 26. The proximal O-ring also facilitates retention of flared proximal end 13 of the tubular member in the intermediate connector.

Depicted in FIG. 2 is an enlarged side view of sheath 11 of FIG. 1 along the line 2—2 highlighting side port 19 of secondary lumen 15, which is formed in outer wall 20 of the tubular member. Taper 22 extending from distal end 12 is also shown.

Depicted in FIG. 3 is a cross-sectional view of sheath 11 of FIG. 2 along the line 3—3 with side port 19 positioned in outer wall 20 of the tubular member. Inner wall 16 separates relatively large, circular main lumen 14 and significantly smaller, crescent-shaped secondary lumen 15.

By way of example, sheath 10 accommodates an 8.5 French outside diameter catheter. Tubular member 11 is approximately 13 cm long and 0.166" in diameter. Main lumen 14 is approximately 0.113" in diameter, and secondary lumen 15 is approximately 0.030" in minor diameter. Inner wall 16 is approximately 0.005" thick, and outer wall 20 is minimally approximately 0.009" thick. Extension tube 37 is a plastic material tube with an outside diameter of approximately 13 French (0.170"). Extension tube 39 is a plastic material tube with an outside diameter of approximately 11 French (0.144").

It is to be understood that the above-described vascular access introducer sheath is merely an illustrative embodiment of the principles of this invention and that other introducer sheaths may be devised by those skilled in the art without departing from the spirit and scope of this invention. It is contemplated that the tubular member comprises any biocompatible semi-rigid material. It is further contemplated that the main and secondary lumens are sized larger or smaller or have other cross-sectional shapes such as square, rectangular, oval, elliptical, crescent, or a combination thereof for accommodating various other clinical applications. It is also further contemplated that other vascular access introducer sheaths include more than two lumens.

What is claimed is:

1. A multiple lumen vascular access introducer sheath comprising:
   a tubular member of an inelastic, semi-rigid plastic material and having a distal end, a proximal end, a main lumen extending longitudinally therethrough and opening at said distal and proximal ends, and a secondary lumen non-coaxially positioned adjacent to and separated from said main lumen for maximizing a cross-sectional dimension of said main lumen, said main lumen having a cross-sectional area sized for passage of a catheter therethrough, said secondary lumen having a cross-sectional area sized significantly less than said cross-sectional area of said maim lumen for passage of a predetermined dose of a fluid therethrough and positioned with respect to said main lumen and shaped.

2. The sheath of claim 1 wherein said tubular member includes an outer wall and wherein said secondary lumen is closed at said distal end of said tubular member and includes a side port in said outer wall near said distal end of said tubular member.

3. The sheath of claim 2 wherein said distal end of said tubular member is tapered.

4. The sheath of claim 2 wherein said plastic material has a molten state.

5. The sheath of claim 1 wherein said plastic material is from a group consisting of fluorinated ethylene propylene and nylon.

6. The sheath of claim 1 wherein said main lumen has a longitudinal axis and wherein said sheath further comprises a hub attached about said proximal end of said tubular member and having a main passage extending longitudinally therethrough and communicating with said main lumen of said tubular member, said main passage of said hub having a longitudinal axis extending therethrough and being at least substantially parallel to said longitudinal axis of said main lumen of said tubular member.

7. The sheath of claim 6 wherein said secondary lumen has a proximal opening recessed from said proximal end of said tubular member.

8. The sheath of claim 7 wherein said hub has a secondary passage communicating with said secondary lumen of said tubular member and extending laterally from said main passage and said secondary lumen of said tubular member.

9. The sheath of claim 8 wherein said hub has a third passage communicating with said main lumen of said tubular member.

10. The sheath of claim 8 wherein said tubular member includes an outer wall and wherein said secondary lumen is closed at said distal end of said tubular member and includes a side port in said outer wall near said distal end of said tubular member.

11. The sheath of claim 1 wherein said tubular member has an inner wall separating said main and secondary lumens.

12. The sheath of claim 1 wherein said cross-sectional area of said main lumen has a circular shape and wherein said secondary lumen of said tubular member has at least a partially crescent shape.

13. The sheath of claim 2 wherein said cross-sectional area of said secondary lumen is approximately fifteen percent of said cross-sectional area of said main lumen.

14. A multiple lumen vascular access introducer sheath comprising:
   a tubular member of an inelastic, semi-rigid plastic material and having a distal end; a proximal end; a main lumen extending longitudinally therethrough, having a longitudinal axis, and opening at said distal and proximal ends; and a secondary lumen extending longitudinally therein and non-coaxially positioned adjacent to and separated from said main lumen for maximizing a cross-sectional dimension of said main lumen, said main lumen having a cross-sectional area sized for passage of a catheter therethrough, said secondary lumen having a cross-sectional area sized significantly less than said cross-sectional area of said main lumen for passage of a predetermined dose of a fluid therethrough; and
   a hub attached about said proximal end of said tubular member and having a main passage extending longitudinally therethrough and communicating with said main lumen of said tubular member, said main passage of said hub having a longitudinal axis and being at least substantially parallel to said longitudinal axis of said tubular member.

15. The sheath of claim 14 wherein said hub has a secondary passage communicating with said secondary lumen and extending laterally from said secondary lumen of said tubular member.

16. The sheath of claim 15 wherein said secondary lumen has a proximal opening recessed from said proximal end of said tubular member.

17. The sheath of claim 14 wherein said main lumen has a circular shape and wherein said secondary lumen has at least a partially crescent shape.

18. The sheath of claim 14 wherein said plastic material has a molten state and is from a group consisting of fluorinated ethylene propylene and nylon.

19. The sheath of claim 15 wherein said tubular member includes an outer wall and wherein said secondary lumen is closed at said distal end of said tubular member and includes a side port in said outer wall near said distal end of said tubular member.

20. A dual lumen vascular access introducer sheath comprising:
   a tube of an inelastic, semi-rigid fluorinated ethylene propylene material and having a tapered distal end; a proximal end; a main lumen extending longitudinally therethrough and having a longitudinal axis, a circular cross-sectional area sized for passage of a catheter therethrough, and an opening at said distal and proximal ends; a secondary lumen closed at said distal end of said tube extending longitudinally therein, recessed from said proximal end of said tube, non-coaxially positioned adjacent to said main lumen, and having a partially crescent-shaped cross-sectional area sized approximately fifteen percent of said circular cross-sectional area of said main lumen for passage of a predetermined dose of a fluid therethrough and for maximizing an inside diameter of said main lumen; an outer wall surrounding said main and secondary lumens, said secondary lumen including a side port in said outer wall near said distal end of said tube; and an inner wall separating said main and secondary lumens; and a hub attached about said proximal end of said tube and having a secondary passage extending laterally from said secondary lumen of said tube and a main passage extending longitudinally therethrough, communicating with said main lumen of said tube and having a longitudinal axis at least substantially parallel to said longitudinal axis of said tube, said hub also having a third passage communicating with said main lumen and extending laterally from said main lumen.

* * * * *